United States Patent [19]

Hackler

[11] Patent Number: 5,696,105
[45] Date of Patent: Dec. 9, 1997

[54] ANTIFUNGAL NAIL COMPOSITION

[76] Inventor: Walter A. Hackler, 1616 Sea Bell Circle, Corona del Mar, Calif. 92625

[21] Appl. No.: 615,420

[22] Filed: Mar. 14, 1996

[51] Int. Cl.$^6$ .................................................. C07D 31/58
[52] U.S. Cl. ........................................................... 514/172
[58] Field of Search ............................................. 514/172

[56] References Cited

U.S. PATENT DOCUMENTS

| | | | |
|---|---|---|---|
| 4,472,393 | 9/1984 | Shapiro | 424/243 |
| 4,755,529 | 7/1988 | Higa et al. | 514/468 |
| 4,775,529 | 10/1988 | Segueira et al. | 424/81 |
| 4,808,610 | 2/1989 | Munayyer et al. | 514/172 |
| 5,346,692 | 9/1994 | Wohlrab et al. | 424/61 |
| 5,391,367 | 2/1995 | DaVincentis et al. | 424/61 |
| 5,420,114 | 5/1995 | Clodman et al. | 514/23 |
| 5,422,361 | 6/1995 | Munayyer et al. | 514/408 |
| 5,422,366 | 6/1995 | Mintzis et al. | 514/474 |
| 5,464,610 | 11/1995 | Hayes, Jr. et al. | 424/61 |

*Primary Examiner*—Rebecca Cook
*Attorney, Agent, or Firm*—Walter A. Hackler

[57] ABSTRACT

The invention relates to a composition treating nail fungus or onychomycosis, which composition includes an effective amount of mometasone furoate and wherein said composition is topically applied to the nail that is to be treated for fungus.

15 Claims, 2 Drawing Sheets

ANTIFUNGAL NAIL COMPOSITION

BACKGROUND OF THE INVENTION

1. Field of the Invention

The invention relates to a composition treating nail fungus or onychomycosis, which composition includes mometasone furoate wherein said composition is topically applied to the nail that is to be treated for fungus.

2. Description of the Art

Onychomycosis is a disease of the nails (unguis) of the fingers and toes caused by *Epidermophyton floccusum*, by several species of Trichophyton or by *Candida albicans*. The nails become opaque, white, thickened, fragile and brittle. It is acknowledged that the therapy of onychomycosis is difficult and protracted. Oral therapy with antimycotics requires months of administration, has only a 50% success rate, and must be closely monitored for side effects.

Unfortunately, such fungal nail infections have proven to be very resistant to treatment. Systemic administration of anti-fungal drugs is hindered by limited blood circulation in the nail bed and poor transport to the nail plate, requiring high dosage levels for long periods of time. Such high drug dosages can have adverse side effects, and it has been found that clearance of the infection is often only temporary. Thus, systemic treatment must often be continued indefinitely.

Topical administration of anti-fungal drugs also suffers certain limitations. The nail plate is a relatively thick structure which inhibits penetration of the drug being applied. Moreover, the topical application of creams, lotions, gels, and the like, is often lost or dissipated in relatively short times. Although attempts have been made to incorporate such topically active anti-fungal drugs into film-forming compositions, e.g., nail polishes or lacquers, to improve drug persistence, such approaches have not proved entirely satisfactory.

Topical use of generally suitable preparations is ineffective, because of inadequate penetration through the nail keratin. A proposal of drilling small holes in the nail to afford the fungicide access to the layers below has been suggested.

Other local measures, mechanical ablation of affected nail areas, is used in practice. Extraction of the nail, particularly where multiple nails are affected, is used but frequently, that is not an acceptable option from the standpoint of the patient.

Moreover, while removal of the nail can improve topical drug treatment, the ability to maintain a constant supply of the drug to the nail bed remains problematic.

For some time, methods have been used which employ a specially formulated antimycotic-containing medicine. Treatment of nails with a high-percentage solution of urea and sodium metabisulfide leads to cleavage of the disulfide linkages and hydrogen bridges of the keratin, enhancing the penetration by the fungicide.

A number of patents and patent applications describe topical compositions, including nail lacquers, for treating fungus of the nails. See for example, U.S. Pat. Nos. 5,346, 692; 5,391,367; 5,420,114; 5,422,366 and 5,464,610. (U.S. Pat. No. 5,464,610 also teaches a plaster composition for treating onychomycosis.)

Thus, it would be desirable to provide improved methods and compositions for treating fungal nail infections. Such methods and compositions should be effective in treating the initial infection as well as inhibiting spread of the infection to other nails and recurrence of the infection after treatment has been completed. It would be desirable to provide treatment methods and compositions which do not rely on the chronic administration of anti-fungal drugs, especially systemic drugs.

U.S. Pat. No. 4,472,393 discloses 3,20-dioxo-1,4-pregnadiene-17 alpha-ol 17-aromatic heterocycle carboxylates, including mometasone furoate. U.S. Pat. No. 4,775,529 discloses a topical formulation of mometasone furoate in a hydro-alcoholic base. U.S. Pat. No. 4,808,610 discloses a cream formulation including mometasone furoate. The above three patents are hereby incorporated by reference for disclosing the active ingredient and topical formulations including such active ingredient that are useful in the method and compositions of the invention.

SUMMARY OF THE INVENTION

The present invention provides method and a composition for fungal nail infections which composition comprises an effective amount of mometasone furoate in a pharmaceutically acceptable vehicle therefore. For example, the pharmaceutical compositions of the invention may comprise from 0.01 to 1.0%, mometasone furoate, by weight, of the total composition. Preferably, the concentration of mometasone furoate may be within a range of from 0.02 to 0.3%, by weight, with a range of from 0.05 to 0.25% by weight, most preferred. The pharmaceutically-acceptable vehicle may comprise a hexylene glycol-containing cream or hydro-alcoholic lotion.

The composition of the present invention may be packaged in a number of containers. It may be supplied in a bottle with a brush applicator similar to a nail polish. It may also be supplied in an applicator tipped bottle. It may also be supplied in a glass and applicator bottle.

Most preferably, the composition utilized in the treatment of onychomycosis or nail fungus is Elocon® mometasone furoate cream 1.0% topical composition that is sold by Schering Plough for Kenilworth, N.J. for dermatological use.

BRIEF DESCRIPTION OF THE DRAWINGS

The advantages and features of the present invention will be better understood by the following description when considered in conjunction with the accompanying drawings in which.

DETAILED DESCRIPTION

Figure 1:
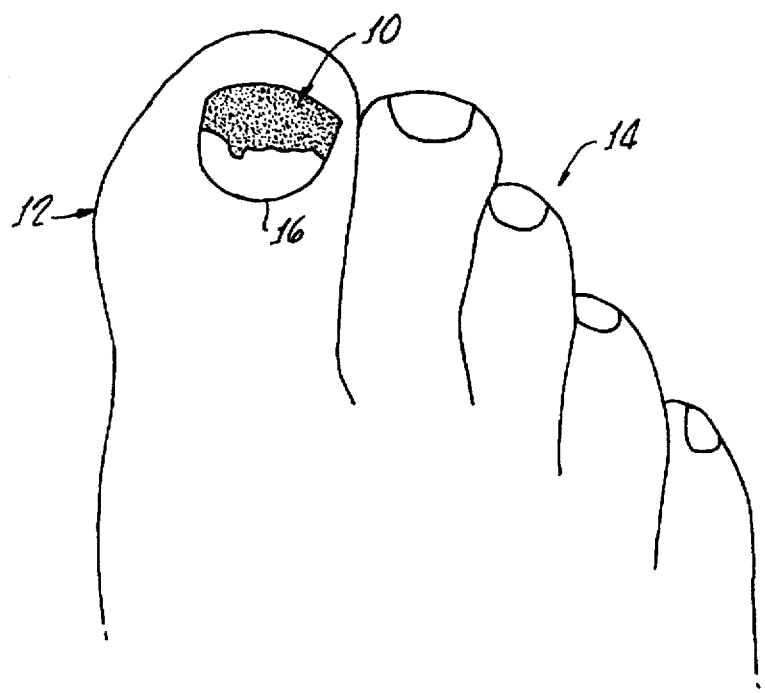
FIG. 1 is a representation of onychomycosis of the nail of the big toe of a human patient to be treated in accordance with the present invention.

Fungal infections which may be treated according to the present invention include infections from yeasts, such as Candida species, most notably albicans; from dermatophytes, such as *Trichophyton mentagrophytes*, *Trichophyton rubrum*, *Trichophyton megninii*, *Trichophyton schoenleinii*, *Trichophyton tonsurans*, and Microsporum species; from molds, such as *Scopulariopsis cephalosporium*, and *Aspergillus fusarium*; from Epidermophyton species; and from *Hendersonula toruloideo*.

Fungal nail infections which may be treated using the methods and compositions of the present invention are usually characterized by tarnished white, yellowed, or blackened nails. The nails will usually pull away from the pink nail bed along the sides or outer edges, and infections are usually exacerbated by not, damp conditions inside the shoes or in environments where hands or feet are continually exposed to moisture. The fungal infections are most commonly found in the toenails and can spread from toe to toe, foot to foot, and foot to hand. Diagnosis of the fungal infections may be microscopic identification and/or culture of the infected areas.

Specific infections which may be treated by the methods and compositions of the present invention include distal subungual onychomycosis (caused by infection with *Candida trichophyton*, Scopularosis, and Aspergillis); superficial white onychomycosis (caused by *Trichophyton mentagrophytes*); proximal white subungual onychomycosis (caused by Trichophyton species); total secondary dystrophic onychomycosis (caused by yeast and Trichophytons); and total dystrophic primary onychomycosis (caused by Candida species).

One aspect of this invention relates to a topical lotion for use in treating onychomycosis or nail fungus.

The present invention provides a mometasone furoate lotion formulation exhibiting high vasoconstrictor activity. The addition of propylene glgcol to a hydro-alcoholic lotion base exhibits significantly higher vasoconstrictor activity than the corresponding lotion without propylene glycol. This increase in vasoconstrictor activity appears to be unique to propylene glycol since substitution of propylene glycol with another glycol, such as hexylene glycol or polyethylene glycol 400, decreases the vasoconstrictor activity of the lotion formulation.

The topical composition comprises an amount effective to treat onychomycosis in a hydro-alcoholic base comprising:

(a) 15 to 50% by weight propylene glycol (b) 20 to 40% by weight isopropyl alcohol (c) 20 to 60% by weight water (d) 0.1 to 3.0% by weight of a thickening agent (e) sufficient buffer to adjust the pH to between 3.0 to 6.0

The lotion of the present invention comprises a therapeutically effective amount of mometasone furoate. The therapeutically effective amount of mometasone furoate is generally an amount of from 0.01 to 1.0% by weight of the total composition. Ranges of 0.02 to 0.2% are particularly suitable with a range of 0.05 to 0.1% by weight being most preferable.

This lotion composition of the present invention may contain a thickening agent to achieve a lotion consistency. Examples of thickening agents useful in the invention are: Carbomer 940, an acrylic acid polymer having an approximate molecular weight of 4,000,000 and available from B. F. Goodrich Chemical Company. Klucel®, a hydroxypropyl cellulose which is a propylene glycol ether of cellulose available from Hercules Inc., Methocel® A, a methyl cellulose (which is a methyl ether of cellulose) available from Dow Chemicals; and Polyquaternium-10 which is a polymeric quaternary ammonium salt of hydroxyethyl cellulose reacted with a trimethyl ammonium substituted epoxide, available from Amerchol Corp. Cosmetic preference or stability considerations will dictate selection of the thickening agent.

The pH of the lotion composition of the present invention is generally in the range of about 3.0 to 6.0 and preferably pH 4.0 to 5.0. Sufficient buffer solution is added to the lotion composition to maintain the pH in the desired range. Examples of buffers useful in the present invention are phosphate buffers, citrate buffers, citrate-phosphate buffers.

A second aspect of the invention provides a cream formulation having cosmetic elegance and outstanding efficacy. The cream formulation is of special value in the topical treatment of onychomycosis or nail fungus.

The cream formulation of the present invention is a unique drug co-solvent-in-oil emulsion for administration to warm-blooded animals, including man, containing as the active anti-inflammatory ingredient an effective amount of mometasone furoate. The internal phase of the emulsion is the drug co-solvent component comprising the hexylene glycol water mixture. In addition to the active ingredient, pharmaceutically acceptable adjuvants, stabilizers, preservatives, whiteners, buffers and surfactants are used in the formulation of this invention.

The cream formulation of the present invention comprises:

0.01 to 0.25% Mometasone Furoate 5 to 20% Hexylene Glycol NF 1.0 to 5.0% Water Purified USP 2.0 to 10.0% White Wax NF 4 to 12% of a lipophilic emulsifier having a HLB below 5

0.7 to 4% of a hydrophilic emulsifier having a HLB above 11

0.2 to 2.0% Titanium Dioxide USP 5 to 20% Aluminum Starch Octenylsuccinate 40 to 70% White Petrolatum USP Sufficient acid is added to adjust the pH of the purified water to pH 2.5±0.2; charged as a 10% w/v solution. Examples of acids which can be utilized in the cream formulation are phosphoric acid, hydrochloric acid, acetic acid, and the like. The preferred acid is phosphoric acid.

In a preferred aspect of the present invention, the formulation comprises:

0.05 to 0.15% Mometasone Furoate 9 to 15% Hexylene Glycol NF 2 to 4% Water Purified USP 4 to 6% White Wax NF 6 to 10% of a lipophilic emulsifier having a HLB below 5

1.2 to 2.5% of a hydrophilic emulsifier having a HLB above 11

0.75 to 1.25% Titanium Dioxide USP 8 to 12% Aluminum Starch Octenylsuccinate 50 to 60% White Petrolatum USP This cream formulation results in an elegant stable, water-washable cream with excellent anti-inflammatory activity. This cream is also self-preserving.

The preferred lipophilic emulsifier is propylene glycol stearate. Other acceptable lipophilic emulsifiers for use in the creams include ethylene glycol monolaurate, ethylene glycol monostearates, propylene glycol monolaurate and glyceryl monoricinolate.

The preferred hydrophilic emulsifier is Ceteareth-20, i.e., polyethylene glycol ether of cetearyl alcohol that conforms generally to the formulas $R(OCH_2CH_2)_nOH$ wherein R represents a blend of cetyl and stearyl radicals and n has an average value of 30. Other acceptable hydrophilic emulsifiers for use in the creams include polyethylene glycol monolaurate, polyethylene glycol distearate, P.O.E. cetyl alcohol, P.O.E. sorbitan monostearate and P.O.E. sorbitan monoleate.

Most preferably, the formulation described above as a preferred aspect of the invention comprises:

0.1% Mometasone Furoate
9 to 15% Hexylene Glycol NF
2 to 4% Water Purified NF
4 to 6% White Wax NF
6 to 10% propylene glycol stearate
1.2 to 2.5% Ceteareth-20
0.75 to 1.25% Aluminum Starch Octenylsuccinate
50 to 60% White Petrolatum USP This most preferred formulation may also comprise stearyl alcohol and titanium dioxide.

The HLB is defined by Griffin, W. C., J. Soc., Cosmetic Chemist, 1,311 [1949] and 5,249 [1949]. The HLB reflects the balance between hydrophilic and lipophilic strength of the emulsifiers. The higher HLB, indicates a stronger hydrophilic tendency of the emulsification system.

Treatment with the compositions of this invention is usually accomplished by applying it to completely cover the affected area. The usual frequency of application is once daily, although adequate maintenance therapy for some patients may be achieved with less frequent application.

The compositions of the present invention are manufactured in a conventional manner by thoroughly mixing the ingredients at ambient or elevated temperatures in order to achieve solubility of ingredients where appropriate. Preferably, in the cream formulation the mometasone furoate, dissolved in a portion of the hexylene glycol/water mixture is added to the oil phase. The ingredients are thoroughly mixed to that the product is homogeneous. Processing equipment suitable for preparing the cream are known in the art and include colloid mills, homogenizers, roller mills, propeller mixers and the like.

All percentages are by weight. The definitions of components whose chemical composition is not immediately clear form the name used, such as "Ceteareth-20" and "Promulgen-G", may be found in the CTFA Cosmetic Ingredients Dictionary, 3rd Edition, published by Cosmetic Toiletry and Fragrance Association, Inc., Washington, D.C.

The following formulation examples illustrate the compositions of the present invention. It will be apparent to those skilled in the art that many modifications thereof may be practical without departing from the purpose and intent of this disclosure.

EXAMPLE 1

A 0.1% mometasone furoate lotion formulation in accordance with the present invention having the following composition.

| Ingredients | mg/g |
|---|---|
| Mometasone furoate | 1.0 |
| Alcohol Isopropyl USP | 400.0 |
| Propylene Glycol USP | 300.0 |
| Hydroxypropylcellulose (Klucel HF) | 1.5 |
| Sodium Phosphate Monobasic Monohydrate R | 2.0 |
| Phosphoric Acid NF (Used to adjust the pH to 4.5 ± 0.1) | |
| Water Purified USP q.s. to make 1 g | |

EXAMPLE 2

An anti-inflammatory cream is prepared from the following ingredients:

| Ingredients | Quantity, mg/g |
|---|---|
| Mometasone Furoate | 1.0 |
| Hexylene Glycol NF | 120 |
| Water Purified USP | 30 |
| White Wax NF | 50 |
| Propylene Glycol Stearate | 80 |
| Stearyl Alcohol and Ceteareth-20 (Promulgen-G) | 70 |
| Titanium Dioxide USP | 10 |
| Aluminum Starch Octenylsuccinate | 100 |
| Phosphoric Acid NF (To adjust the Ph of the purified water to Ph 2.5 ± 2; charged as a 10% w/v solution) | |
| White Petrolatum USP | 539 |

The cream formulation is prepared in a procedure including the following steps:

1. In a suitable vessel charge the white petrolatum, white wax, propylene glycol stearate and Promulgen-G. Melt and heat to 70° C. with agitation until a homogenous melted mixture is obtained.
2. In a separate vessel, prepare a 10% w/v phosphoric acid solution.
3. Charge the purified water to a suitable vessel and adjust the Ph of the water to about 2.5 with 10% phosphoric acid solution.
4. Charge the hexylene glycol to the acidified water and adjust the Ph to 4.0 by addition of the 10% phosphoric acid solution, only if necessary.
5. Dissolve the mometasone furoate in approximately 90% of the hexylene glycol/water at 60°–65° C. Heat the solution to 70° C. and charge to the mixture prepared in Step 1. Mix to achieve adequate emulsification at 70° C.
6. Rinse containers used for the active solution with the remaining 10% hexylene glycol/water and add rinse to the emulsions prepared in Step 5.
7. Charge the titanium dioxide and aluminum starch octenylsuccinate in small portions to Step 5 at 70° C. and mix for at least twenty minutes.
8. Cool the batch to approximately 25°°C. with appropriate mixing and add to appropriate containers.

EXAMPLE 3

An anti-inflammatory cream is prepared from the following ingredients:

| Ingredients | Quantity, mg/g |
|---|---|
| Mometasone Furoate | 0.5 |
| Hexylene Glycol NF | 60.0 |
| Water Purified USP | 15.0 |
| White Wax NF | 60.0 |
| Propylene Glycol Stearate | 70.0 |
| Stearyl Alcohol and Ceteareth-20 (Promulgen-G) | 60.0 |
| Titanium Dioxide USP | 10 |
| Aluminum Starch Octenylsuccinate | 100 |
| Phosphoric Acid NF (To adjust the Ph of the purified water to Ph 2.5 ± 0.2; charged as a 10% w/v solution. | |
| White Petrolatum USP | 624.5 |

The procedure for preparing the cream is prepared form the following ingredients.

EXAMPLE 4

| Ingredients | Quantity, mg/g |
|---|---|
| Mometasone Furoate | 1.0 |
| Hexylene Glycol NF | 120.0 |
| Water Purified USP | 30.0 |
| Microcrystalline Wax | 50.0 |
| Propylene Glycol Stearate | 80.0 |
| Stearyl Alcohol and Ceteareth-20 (Promulgen-G) | 70.0 |
| Titanium Dioxide USP | 8.0 |
| Aluminum Starch Octenylsuccinate | 120.0 |
| Hydrochloric Acid NF (To adjust the Ph of the purified water to Ph 2.5 ± 0.2; charged as a 10% w/v solution. | |
| White Petrolatum USP | 521.0 |

The procedure for preparing the cream is as described in Example 2.

EXAMPLE 5

| Ingredients | Quantity, mg/g |
|---|---|
| Mometasone Furoate | 1.0 |
| Hexylene Glycol NF | 120.0 |
| Water Purified USP | 30.0 |
| White Wax NF | 50.0 |
| Sorbitan Trioleate | 80.0 |
| Stearyl Alcohol and Ceteareth-20 (Promulgen-G) | 70.0 |
| Titanium Dioxide USP | 5.0 |
| Aluminum Starch Octenylsuccinate | 150.0 |
| Phosphoric Acid NF (To adjust the Ph of the purified water to Ph 2.5 ± 0.2; charged as a 10% w/v solution. | |
| White Petrolatum USP | 494.0 |

EXAMPLE 6

Various patients are treated for nail fungus with any of the compositions of Examples 1 through 5 with the following results.

Patient A: Female patient in mid-forties has onychomycosis of a fingernail. After six weeks of treatment, she has a 2 mm wide clear (i.e. uninfected) zone of new nail at the base of the nail. The treatment has arrested fungal growth, and the new growth (the clear zone) is uninfected. At week 12 of treatment, the clear zone is 4 mm wide, and the patient is continuing to use the treatment.

Patient B: Female patient in her early fifties has an onychomycotic infection of five toenails on the same foot. After 6 weeks of treatment, the nails of the four small toes shows dramatic clearing. The nail on the great toe has been fully involved, and new nail appears to be growing under the old (infected) nail plate.

Patient C: Female patient in mid-thirties had repetitive episodes of onychomycosis of the fingernails. Treatment with any of the above-described composition is commenced. When the treatment begins, only one nail is infected. Only that infected nail is treated with the above-described formulations. After four weeks of treatment, the infection is arrested in that nail (as shown by a clear zone of new growth, uninfected nail). Furthermore, the infection has not spread to other nails. At ten weeks of treatment, the infected nail is virtually clear (100% uninfected), and no other nails had become infected.

Figure 2:
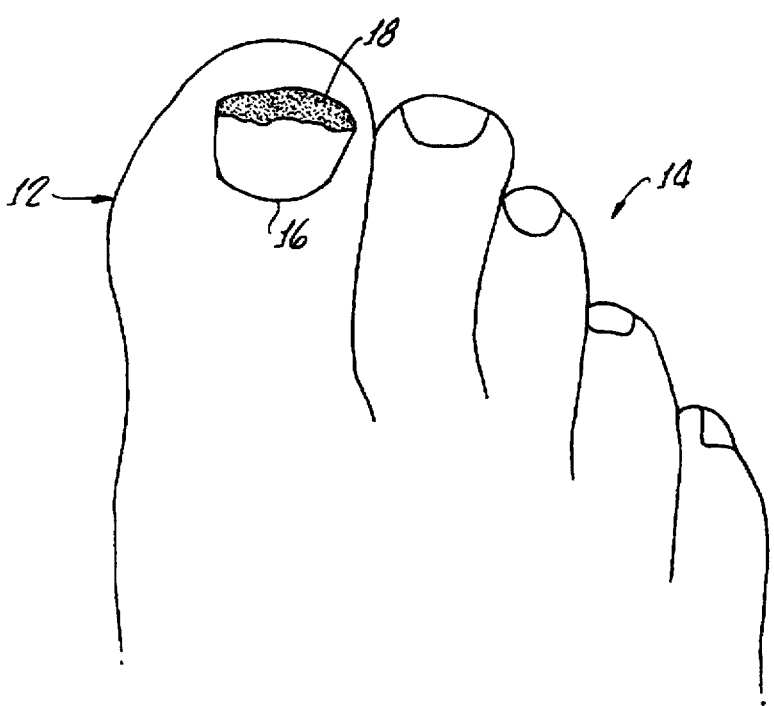
FIG. 2 is a representation of the treatment of the onychomycosis of the big toe shown in FIG. 1 after topical application of Elocon® for a period of 10 weeks.
Figure 3:
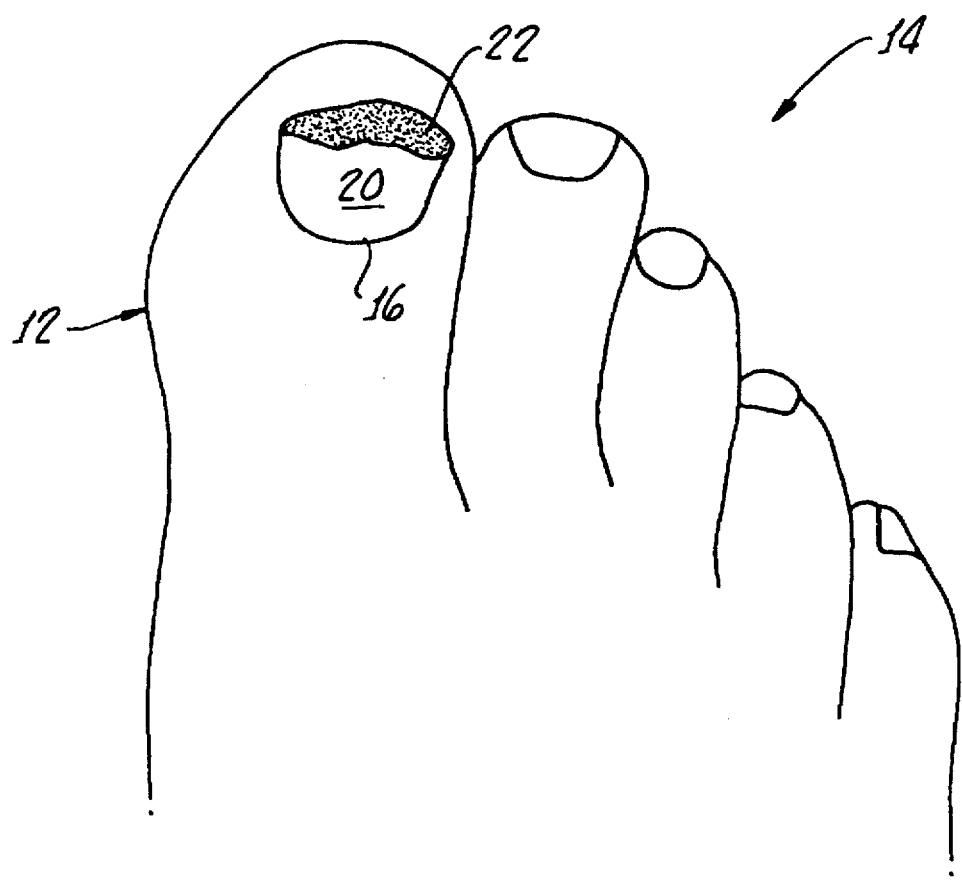
FIG. 3 is a representation of the treatment of the onychomycosis of the big toe shown in FIG. 1 after topical application of Elocon® for a period of 20 weeks.

Patient D: Male patient in his mid-fifties had onychomycotic infection 10 of the big toenail 12 each foot 14, a representation of one foot 14 being shown in FIG. 1. As shown in FIG. 1, the infection 10 extended to within about 2 mm of the cuticle 16. For 10 weeks he applied Elocon® brand of mometasone furoate cream 0.1% to the upper nail surface of infected toes twice daily. After the 10 week period, a clear zone of about 6 mm extending from the cuticle was seen, as represented in FIG. 2 to the infected area 18. After 20 weeks, the zone extended about 10 mm from the cuticle. The result after 20 weeks, showing that the infection was arrested, is shown in the FIG. 3 wherein the area 20 is the clear nail zone, extending about 10 mm from the cuticle 16. The shaded area 22 is the previously infected zone of the toenail which, is growing away from the cuticle 16 and will eventually be scissored from the healthy nail that extends from the cuticle. It should be appreciated that while the formulation, in accordance with the present invention, may not directly "kill" the infection, it makes the nail inhospitable for fungal growth. As growth of the nail continues, new nail growth, made inhospitable to infection, or fungal, effectively forms a complete healthy nail Although the foregoing invention has been described in detail for purposes of clarity of understanding, it will be obvious that certain modifications may be practiced within the scope of the appended claims. For example the various 3, 20 dioxo-1, 4 pregnadien-17 alpha-ol 17 aromatic heterocyclic carboxylates, described in U.S. Pat. No 4,472,393, i.e.

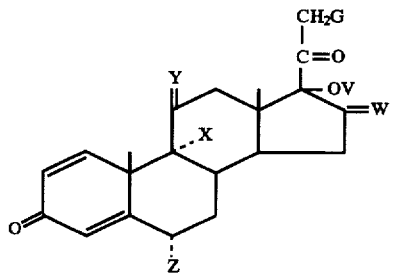

wherein X is a member selected from the group consisting of hydrogen and halogen having an atomic weight less than 100;

Y is a member selected from the group consisting of (H,H) provided X is hydrogen, oxygen, (H, betaOH, and (H, beta-halogen) provided X is chlorine or bromine, said beta-halogen having an atomic weight of less than 100, and being at least as electronegative as X;

Z is hydrogen, $CH_3$, chlorine, or fluorine;

V is an acyl radical of an aromatic heterocyclic carboxylic acid selected from the group consisting of thiophenacarboxylic acid, pyrrolecarboxylic acid and furancarboxylic acid, and methyl and halogen-substituted derivatives thereof;

W is a member selected from the group consisting of (H, H); (H, lower alkyl); (H, $OV_1$) wherein $V_1$ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is a member selected from the group consisting of hydrogen, lower alkyl, fluorine, and chlorine; G is hydrogen, a halogen having an atomic weight less than 100, or $OV_2$ wherein $V_2$ is a member selected from the group consisting of hydrogen, an acyl radical of a hydrocarbon-carboxylic acid having up to 12 carbon atoms, benzoic acid substituted by a halogen or methoxy group, retinoic acid, isonicotinic acid, and the acid radical of phosphoric acid and mono- and dialkali and alkaline earth metal salts thereof; and the 6-dehydro and 1,2-dihydro analogs of the foregoing.

In particular, the 17 furoyl and 17 thenoyl esters of mometasone are useful in the method of the present invention.

Although there has been hereinabove described a method of treating fungal infection in accordance with the present invention, for the purpose of illustrating the manner in which the invention maybe used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method of treating fungal infection or onychomycosis of the nails in a patient in need thereof by topically applying a composition consisting essentially of an effective amount of a 3,20-dioxo-1, 4-pregnadiene wherein said 3,20-dioxo-1, 4-pregnadiene is mometasone furoate in a pharmaceutically acceptable vehicle.

2. The method of claim 1 wherein said composition consists essentially of from 0.01 to 1.0%, by weight, mometasone furoate.

3. The method of claim 2 wherein said composition is a lotion.

4. The method of claim 3 wherein said pharmaceutically-acceptable vehicle is a hydro-alcoholic base comprising 15 to 50% by weight of propylene glycol; 20 to 40% by weight of isopropyl alcohol; 20 to 60% by weight water; 0.1 to 3.0% by weight of a thickening agent, and sufficient buffer to maintain the pH of the composition within the range of 3.0 to 6.0.

5. The method of claim 2 wherein said composition consists essentially of:

| Ingredients | Concentration mg/g |
| --- | --- |
| Mometasone furoate | 1.0 |
| Alcohol Isopropyl USP | 400.0 |
| Propylene Glycol USP | 300.0 |
| Hydroxypropyl Cellulose (Klucel HF) | 1.5 |
| Sodium Phosphate Monobasic Monohydrate R | 2.0 |
| Phosphoric Acid NF (To adjust the pH to 4.5 ± 0.1.) | |
| Water Purified USP q.s. to make | 1 g |

6. The method of claim 4 wherein the thickening agent is an acrylic acid polymer.

7. The method of claim 4 wherein the thickening agent is hydroxypropyl cellulose.

8. The method of claim 2 wherein said composition is a cream.

9. The method of claim 8 wherein said composition consists essentially of:

0.01 to 0.25% Mometasone Furoate 5 to 20% hexylene glycol 1.0 to 5.0% water 2.0 to 10.0% white wax 4 to 12% of a lipophilic emulsifier having a HLB below 5

0.7 to 4% of a hydrophilic emulsifier having a HLB above 11

0.2 to 2.0% Titanium dioxide 5 to 20% aluminum starch octenylsuccinate 40 to 70% white petrolatum sufficient acid to adjust the pH of the water to pH 2.5+0.2.

10. The method of claim 9 wherein said composition consists essentially of:

0.05 to 0.15% Mometasone Furoate 9 to 15% hexylene glycol 2 to 4% water purified 4 to 6% white wax 6 to 10% of a lipophilic emulsifier having a HLB below 5

1.2 to 2.5% of a hydrophilic emulsifier having a HLB above 11

0.75 to 1.25% Titanium dioxide 8 to 12% aluminum starch octenylsuccinate 50 to 60% white petrolatum sufficient acid to adjust the pH of the water to pH 2.5±0.2.

11. The method of claim 8 wherein the acid utilized to adjust the pH of the water is selected from the group consisting of phosphoric acid, hydrochloric acid and acetic acid.

12. The method of claim 8 wherein the lipophilic emulsifier is selected from the group consisting of propylene glycol stearate, ethylene glycol monolaurate, ethylene glycol monostearate, propylene glycol monolaurate, and glyceryl monoricinolate.

13. The method of claim 12 wherein the hydrophilic emulsifier is stearyl alcohol and ceteareth-20, polyethylene glycol monolaurate, polyethylene glycol distearate, P.O.E. cetyl alcohol, P.O.E. sorbitan monostearate or P.O.E. sorbitan monooleate.

14. The method of claim 8 wherein said composition consists essentially of (in mg/g):

Mometasone Furoate 1.0

Hexylene Glycol NF 120.0

Water Purified USP 30.0

White Wax NF 50.0

Propylene Glycol Stearate 80.0

Stearyl Alcohol and Ceteareth-20 70.0 (Promulgen-G)

Titanium Dioxide USP 10.0

Aluminum Starch Octenylsuccinate 100.0

White Petrolatum USP 539.0

Sufficient Phosphoric Acid NF to adjust the pH of the water to pH 2.5±0.2.

15. A method of making unguis inhospitable to the growth of fungal infection in a patient in need thereof by applying a composition consisting essentially of an effective amount of mometasone furoate in a pharmaceutically-acceptable vehicle to the unguis.

* * * * *